United States Patent [19]

Frimberger

[11] Patent Number: 5,109,833
[45] Date of Patent: May 5, 1992

[54] HEART MASSAGE AND ARTIFICIAL RESPIRATION DEVICE

[76] Inventor: Eckart Frimberger, Tristanstrasse 21, D-8000 München, Fed. Rep. of Germany

[21] Appl. No.: 540,154

[22] Filed: Jun. 19, 1990

[30] Foreign Application Priority Data

Jun. 19, 1989 [DE] Fed. Rep. of Germany ....... 3919956

[51] Int. Cl.⁵ ............................................. A61H 31/00
[52] U.S. Cl. .................................. 128/28; 128/205.13; 128/205.14; 128/205.16; 128/205.23; 92/43; 92/44
[58] Field of Search ............. 128/30.2, 30, 28, 205.13, 128/205.16, 205.14, 205.23–205.25, 202.13, 202.16; 92/41, 44, 43

[56] References Cited

U.S. PATENT DOCUMENTS

| | | | |
|---|---|---|---|
| 2,070,960 | 2/1937 | Phillips | 92/43 |
| 2,399,643 | 5/1946 | Krieselman | 128/205.3 |
| 4,349,015 | 9/1982 | Alferness | 128/28 |
| 4,664,098 | 5/1987 | Woudenberg et al. | 128/30.2 X |

Primary Examiner—Robert Bahr
Assistant Examiner—J. Doyle
Attorney, Agent, or Firm—Scully, Scott, Murphy & Presser

[57] ABSTRACT

The invention relates to a heart massage and artificial respiration device comprising a patient adapter, a compressible, elastically re-expanding bellows or the like adapted to be placed on the thorax of the patient, an air intake valve associated with the bellows, a patient valve between the bellows and the patient adapter and a normally closed pressure relief valve which, after completion of the compression step, is necessarily opened mechanically, wherein to achieve the objects of simplification, more economical manufacture, simple assembly, cleaning and maintenance, and for absolutely reliable functioning under rough usage both in and out of hospitals, the air intake valve and the pressure relief valve are combined to form a universal valve.

20 Claims, 2 Drawing Sheets

5,109,833

HEART MASSAGE AND ARTIFICIAL RESPIRATION DEVICE

TECHNICAL FIELD OF THE INVENTION

The invention relates to a combined heart massage and artificial respiration device.

BACKGROUND OF THE INVENTION AND PRIOR ART

A device of this kind is described in DE-OS 36 17 327.

With this device it is possible for one person to carry out both heart massage and artificial respiration so that when using the device the heart can be massaged reliably when the lungs are in the exhaled state.

However, in this device the air intake valve and the pressure relief valve are separate valves. As a result the device is still complicated, expensive to manufacture, difficult to assemble, to clean and to maintain, and when subjected to rough usage outside of hospitals it may not function reliably, which is not acceptable from the patient's point of view.

OBJECT OF THE INVENTION

It is therefore an object of the present invention to modify a device of this kind so that it is simpler, more economical to manufacture, easy to assemble, to clean and to maintain and can function absolutely reliably even in the case of rough usage inside and outside hospitals.

SUMMARY OF THE INVENTION

According to the invention, the air intake valve through which the air is sucked in and the pressure relief valve are combined with a common unitary valve sleeve.

By this means the above object is achieved and the disadvantages of the older device are avoided.

Further features of the invention are set forth in the subclaims.

BRIEF DESCRIPTION OF THE DRAWINGS

An exemplary embodiment of the invention is shown in the drawings and will now be described. In the drawings

DETAILED DESCRIPTION OF A PREFERRED EXEMPLARY EMBODIMENT OF THE INVENTION

Figure 1:
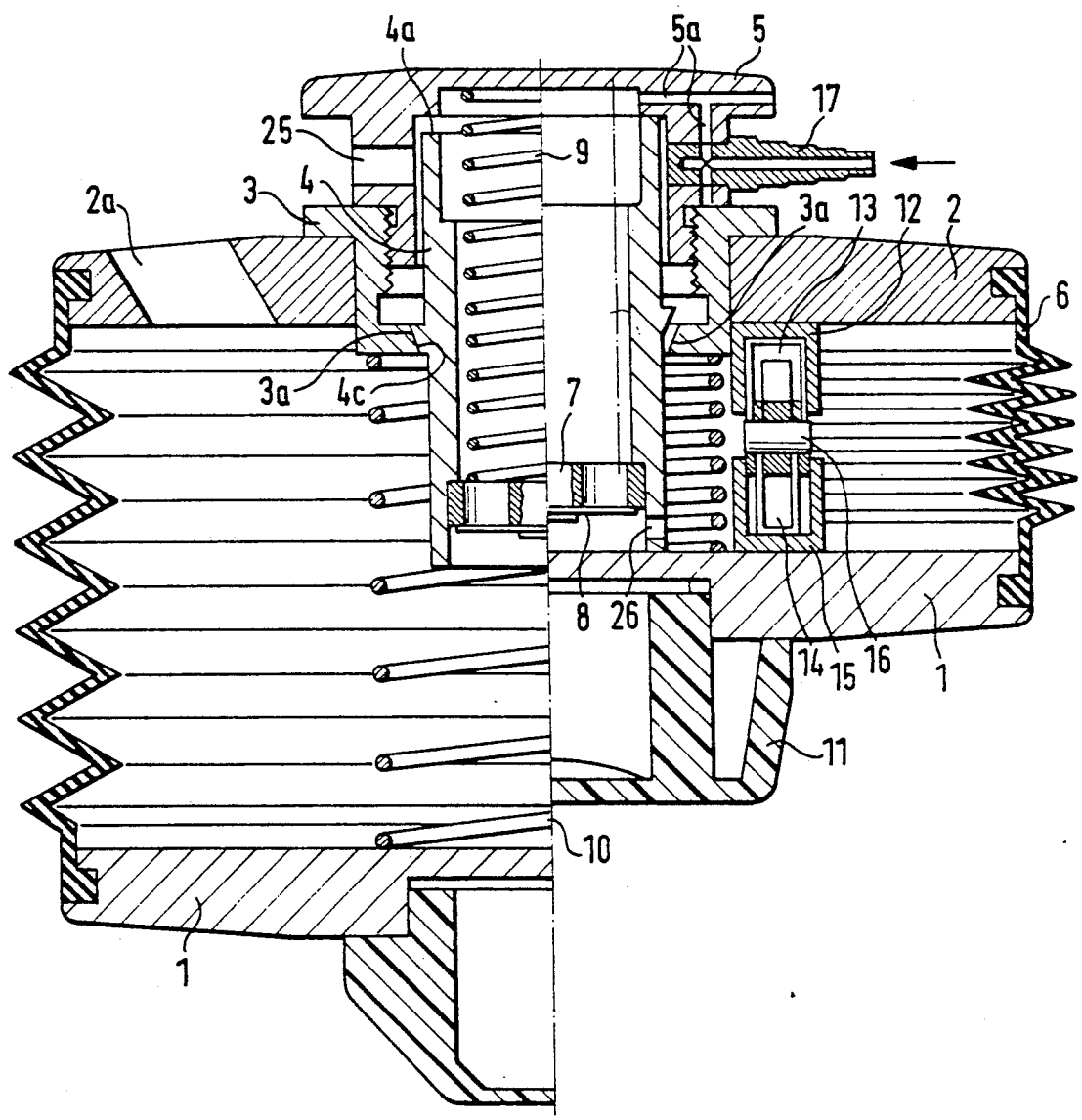
FIG. 1 shows an axial section through the device according to the invention, to the left of the centre line in the relaxed position and to the right thereof in the compressed position.

In the drawings the numeral 1 indicates a bottom plate, on which the entire device is assembled, the underside of which carries a pressure piece 11 to be placed on the thorax of the patient to be resuscitated and massaged. Located on the upper side is a cover plate 2 which has a bore 2a for connecting a hose which leads to a patient adapter 30, such as a breathing mask or intubation tube, by way of a patient valve 30. Inserted in the cover plate 2 is a flanged bushing 3 which has a hole centrally through its underside on which is formed a preferably conical valve seat 3a. A cap 5 which has lateral bores 25 for supplying air is screwed into the bushing 3. A connecting piece 17 for supplying oxygen is inserted laterally into the side of the cap 5 and the supplied oxygen continues through bores 5a therein. Located within the cap 5 and the bushing 3 is a sleeve 4 formed as a universal valve. It is constantly pushed downwards by a helical pressure spring 9, or other suitable spring, so that as a rule, the external and preferably conical thickening 4c is seated on the valve seat 3a and forms a first pressure relief valve. The pressure relief valve 3a, 4c also acts like a safety valve when a pressure which corresponds to the force exerted by the spring 9 is exceeded. The upper end 4a of the sleeve 4 together with the inside of the cap 5 forms a second valve. A third valve is formed by the lower end 4b of the sleeve 4 together with the inside of the bottom plate 1. In addition there is a lateral opening 26 in the sleeve 4. The sleeve 4 carries inside it a perforated valve plate 7 that can be sealed by a small elastic plate or flap 8 that bears thereon so that air and/or oxygen can only flow through from the top to the bottom. Numeral 10 indicates a pressure spring, preferably a helical spring, which is inserted between the bushing 3 and the bottom plate 1 so that, after compressing the bellows 6, which is sealingly fixed between the bottom plate 1 and the cover plate 2, and after removing the pressure from the cover plate 2, the bellows 6 expands again.

Figure 2:
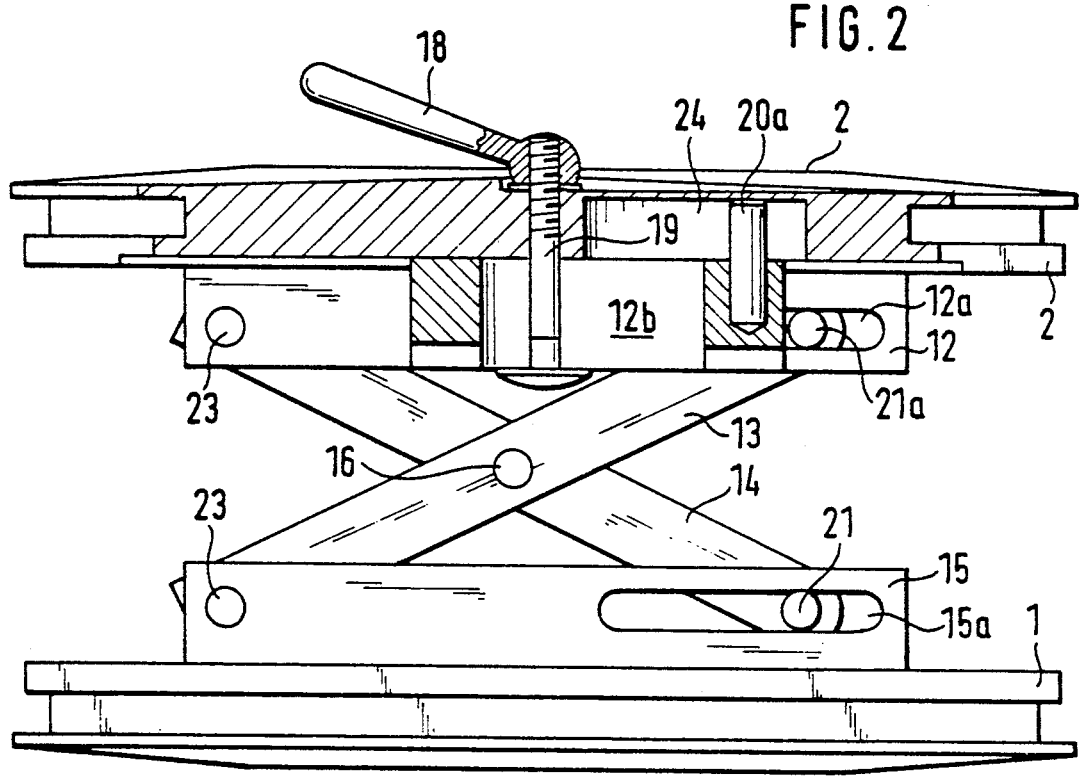
FIG. 2 shows a side elevation of the device, omitting the expansion bellows, to illustrate the guide means and the stroke limiting device.

Since the bellows 6 is not intrinsically stiff and can therefore deflect laterally, which would impair its functioning, a guide means is necessary. As shown in FIG. 2 this comprises a scissor arrangement comprising two arms 13, 14 which are linked in the middle at 16 so that they can adjust mutually in one plane like a pair of scissors. One end of each of the arms 13, 14 is connected pivotably by means of a linkage 23 to an upper and lower guide rail 12 and 15 respectively so that when pressure is applied to the cover plate 2 the scissors can be pushed closed against the bottom plate 1 and guide the cover plate 2 in a straight line. The arm 13 is guided by means of a pin 21a in a slit 12a in the upper guide rail 12 and the arm 14 is guided by a pin 21 in a slit 15a in the lower guide rail 15. A return spring 22 pulls the slide 20 back into the starting position defining the maximum stroke. Three of these guide means can be provided, arranged in a triangle.

Figure 3:
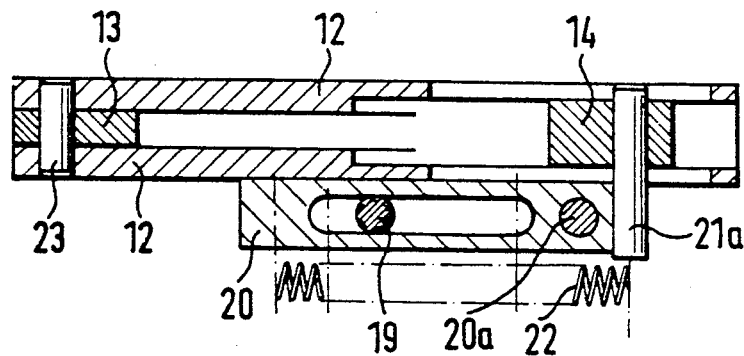
FIG. 3 shows a plan view of the stroke limiting device.

To adjust the stroke, and thus the volumetric displacement of the device, a stroke limiting device is provided which can be seen in side elevation in FIG. 2 and in a plan view in FIG. 3. For this purpose a slide 20 is provided which is arranged to slide on the upper guide rail 12. The front end of the slide bears, on the right hand side of FIGS. 2 and 3, against the pin 21a of the arm 13, which is longer than the pin 21. To adjust the stroke the slide 20 is displaced into the desired setting and is secured by means of an adjusting screw 19 with a clamping lever 18. The setting of the slide 20 can be seen from an indicating pin 20a which slides in a slit 24 in the upper cover plate 2, said slit 24 having a suitable slit cover and either the suitable slit cover or the cover plate 2 carrying a scale from which the setting of the slide 20 and thus the stroke and the displacement can be read from outside.

This device operates in the following manner:

In the normal, relaxed position all components assume the position shown on the left hand side in FIG. 1.

The device is filled with respirable gas—air, oxygen or a mixture thereof. When the device is placed with the pressure piece 11 on the thorax of the patient the person giving first aid can displace the cover plate 2 towards the bottom plate 1 by applying pressure on the cap 5. Since the cap 5 is securely screwed into the bushing 3 and can therefore not be displaced longitudinally, the first pressure relief valve 3a, 4c is closed by the spring 9 in the rest position of the device and while the cover plate 2 is being pushed down. It opens when there is excess pressure and thus functions as a pressure relief valve. With further movement downwards the lower end 4b of the sleeve 4 first comes up against the bottom plate 1 to close the third valve 4b, and the first valve 3a, 4c is opened. In this way the pressure between the interior of the bellows and the air outside is equalised. The upper end 4a of the sleeve 4 then comes up against the inside of the cap 5 and thereby closes the second valve 4a, 5. As a result of the movement of the cover plate 2 downwards the air in the bellows 6, which may be enriched with oxygen or be pure oxygen is compressed and is forced through the bore 2a along a path (not shown) via a hose and the patient valve which may, for example, be near the cover plate 2, and into the lungs of the patient. On reaching maximum compression of the bellows 6 and its contents the lower end 4b of the sleeve 4 comes up against the bottom plate 1 to close the third valve. The simultaneous opening of the first valve 3a, 4c results in a drop in pressure in the space formed by the device, patient valve, hose and respiratory paths of the patient. Owing to this drop in pressure the patient valve opens outwardly and the patient breathes out via the patient valve.

In addition, as a result of the communication between the interior of the bellows and the air outside, the space left inside the bellows after pushing the cover plate 2 down and which cannot be compressed any further is filled with oxygen via the $O_2$-connecting piece 17. The oxygen follows the path via the connecting piece 17, bore 5a, interior of the sleeve 4 and the lower lateral bore in the sleeve 4 into the interior of the bellows.

It is now possible to massage the patient's thorax and thus his heart by way of the relatively rigid device by applying a plurality of blows to the cap 5.

On again releasing the cap 5 the bellows 6 expands under the pressure of the spring 10 and air is sucked in through the openings 25 and the valve 7, 8 which opens automatically.

In the rest position oxygen flows via the connecting piece 17 and the bores 5a in the cap 5 into the device and out via the bores 25. Thus it does not flow through the bellows chamber. If the heart massage device is pressed down the lower end 4b of the sleeve 4 strikes the interior of the bottom plate 1, whereupon the valve 3a, 4c opens and the valve 4a, 5 closes. Oxygen that has been introduced flows from the connecting piece 17 via the bores 5a in the cap 5 into the interior of the sleeve 4, through the valve plate 7 and the automatically opening valve flap 8 and the lateral opening 26 into the chamber of the bellows 6. Air from the inside flows out via the valve 3a, 4c.

It can be seen that with this simplified device not only is it possible for one person alone to carry out the two life saving procedures of respiration and massaging the heart immediately after one another and in combination, but also the location is just as unimportant as is the other equipment at the site of treatment.

The guide means ensures satisfactory operation even if the force exerted on the cap 5 is applied asymmetrically. By means of the stroke limiting device the correct respiratory amount for the conditions can be set.

What is claimed is:

1. A heart massage and artificial respiration device comprising a patient adapter, a compressible, elastically re-expanding bellows adapted to be placed on the thorax of the patient, an air intake valve coupled to the bellows, a patient valve coupled between the bellows and the patient adapter, and a normally closed pressure relief valve which, after completion of compression of the bellows, is mechanically opened, characterized in that said air intake valve and said pressure relief valve comprising a common unitary cylindrical sleeve having a central through-flow.

2. A device according to claim 1, further including a cap sealing the device at one end, and an $O_2$-inlet allowing $O_2$ to flow by one end of said cylindrical sleeve and inside of said cap.

3. A device according to claim 1, further including a bushing mounted around said cylindrical sleeve, and wherein said pressure relief valve comprises a conical thickening around the outside of said cylindrical sleeve which cooperates with a conical valve seat on said bushing.

4. A device according to claim 1, further including a cap sealing the device at one end, and wherein a spring biases said cylindrical sleeve away from said cap.

5. A device according to claim 1, further including a bottom plate for the device, and wherein said pressure relief valve is opened mechanically by one end of said cylindrical sleeve bearing against the inside of said bottom plate.

6. A device according to claim 5, wherein a further valve is formed by one end of said cylindrical sleeve bearing against the inside of said bottom plate, and a lateral opening in said cylindrical sleeve.

7. A device according to claim 2, wherein said cylindrical sleeve carries an elastic seal at at least one of its ends.

8. A device according to claim 1, wherein said cylindrical sleeve mounts an internal valve plate forming a seat for a one way elastic flap valve which functions as an automatically opening one way valve.

9. A device according to claim 1, further including a guide means for guiding and securing compression and expansion movements of said bellows and actuating movements of said cylindrical sleeve.

10. A device according to claim 9, wherein said guide means comprises a two-armed scissor arrangement.

11. A device according to claim 10, wherein said device includes a cover plate arranged at one end of the bellows and a bottom plate for the device, and wherein said two arms of the scissors are linked at one end to an upper and a lower guide rail respectively arranged on said cover plate and said bottom plate.

12. A device according to claim 11, wherein said two arms are guided at their other ends by means of pins movable in slits in said guide rails.

13. A device according to claim 12, further including a stroke limiting device for adjusting the stroke and the volumetric displacement of the device.

14. A device according to claim 13, wherein said stroke limiting device includes a slide which is arranged on said upper guide rail, and one end of the slide bears against one said pin movable in a slit in said guide rail.

15. A device according to claim 14, wherein said slide can be held in a position by means of an adjusting screw and a clamping lever.

16. A device according to claim 14, wherein an upwardly projecting indicating pin is provided on said slide which protrudes through a slit in the cover plate.

17. A device according to claim 16, wherein a slit cover is provided for said slit in the cover plate.

18. A device according to claim 17, wherein a scale is provided on the slit cover or in the immediate vicinity thereof, on which said indicating pin shows the setting of the stroke and of the volumetric displacement.

19. A device according to claim 14, further including a return spring for said slide.

20. A device according to claim 1, including a means for defining lateral opening in said cylindrical sleeve, and a connecting piece for supplying oxygen to the inside of said cylindrical sleeve, and through said lateral opening in said cylindrical sleeve.

* * * * *